United States Patent
Mikulski

(10) Patent No.: US 11,672,720 B2
(45) Date of Patent: Jun. 13, 2023

(54) REHABILITATION DEVICE

(71) Applicant: EGZOTECH SPOLKA Z O.O., Gliwice (PL)

(72) Inventor: Michal Mikulski, Gliwice (PL)

(73) Assignee: EGZOTECH SPOLKA Z O.O., Gliwice (PL)

(*) Notice: Subject to any disclaimer, the term of this patent is extended or adjusted under 35 U.S.C. 154(b) by 1086 days.

(21) Appl. No.: 14/888,094

(22) PCT Filed: Jan. 16, 2014

(86) PCT No.: PCT/IB2014/058339
§ 371 (c)(1),
(2) Date: Oct. 30, 2015

(87) PCT Pub. No.: WO2014/111882
PCT Pub. Date: Jul. 24, 2014

(65) Prior Publication Data
US 2016/0199245 A1    Jul. 14, 2016

(30) Foreign Application Priority Data

Jan. 16, 2013 (PL) .......................... 406866
Jan. 17, 2013 (PL) .......................... 402465

(51) Int. Cl.
*A61H 1/00* (2006.01)
*A63B 21/005* (2006.01)
(Continued)

(52) U.S. Cl.
CPC ............. *A61H 1/008* (2013.01); *A61B 5/389* (2021.01); *A63B 21/0058* (2013.01);
(Continued)

(58) Field of Classification Search
CPC ...................... A61H 1/008; A61H 2230/60; A63B 21/4047; A63B 21/0058; A63B 23/0355;
(Continued)

(56) References Cited

U.S. PATENT DOCUMENTS 2,777,439 A * 1/1957 Tuttle ...................... A61H 1/02
482/118
4,772,015 A * 9/1988 Carlson .................. A63B 23/12
482/902
(Continued)

FOREIGN PATENT DOCUMENTS

WO          9526701 A1   10/1995
WO         02096274 A2   12/2002
WO       2014116128 A1    7/2014

*Primary Examiner* — Steven O Douglas
(74) *Attorney, Agent, or Firm* — Andrzej Malarz, Esq.

(57) ABSTRACT

A device for rehabilitating patients especially with peripheral nervous system paralysis. The rehabilitation device comprising a remote control terminal, a base, an arm mounted to a column with adjustable height containing an motor propelling the arm and at least two electrodes of the electromyography (EMG) sensor according to the disclosure is characterized in that the actuator (7) enables the extension (4) to move within the angular range of 360°, while the EMG signal from the sensor connected to the muscle or muscles of the patient is transmitted to the network of the motor controlling module (2) and then further by radio or cable connection to a remote control terminal (1).

16 Claims, 3 Drawing Sheets

(51) Int. Cl.
*A63B 71/00* (2006.01)
*A63B 23/035* (2006.01)
*A63B 24/00* (2006.01)
*A63B 21/00* (2006.01)
*A61B 5/389* (2021.01)
*A63B 71/02* (2006.01)

(52) U.S. Cl.
CPC ...... *A63B 21/4047* (2015.10); *A63B 23/0355* (2013.01); *A63B 23/03508* (2013.01); *A63B 24/0062* (2013.01); *A63B 24/0087* (2013.01); *A63B 71/0054* (2013.01); *A61H 2230/60* (2013.01); *A63B 2024/0068* (2013.01); *A63B 2024/0093* (2013.01); *A63B 2024/0096* (2013.01); *A63B 2071/0072* (2013.01); *A63B 2071/025* (2013.01); *A63B 2210/50* (2013.01); *A63B 2225/20* (2013.01); *A63B 2230/605* (2013.01)

(58) Field of Classification Search
CPC ............ A63B 24/0062; A63B 24/0087; A63B 71/0054; A63B 2024/0068; A63B 2024/0093; A63B 2024/0096; A63B 2071/0072; A63B 2071/025; A63B 2210/50; A63B 2225/20; A63B 2230/605

See application file for complete search history.

(56) References Cited

U.S. PATENT DOCUMENTS

| | | | |
|---|---|---|---|
| 5,722,420 A | 3/1998 | Lee | |
| 6,599,255 B2* | 7/2003 | Zhang | A61H 1/02 600/587 |
| 9,044,630 B1* | 6/2015 | Lampert | A63B 23/035 |
| 9,193,065 B2* | 11/2015 | Wang | B25J 5/00 |
| 10,018,298 B2* | 7/2018 | Goldish | F16M 11/42 |
| 2002/0135188 A1* | 9/2002 | Chang | E05B 47/0002 292/144 |
| 2002/0183655 A1* | 12/2002 | Zhang | A61H 1/02 600/587 |
| 2004/0106881 A1 | 6/2004 | McBean et al. | |
| 2006/0253052 A1 | 11/2006 | Cordo | |
| 2009/0259338 A1 | 10/2009 | Tong et al. | |
| 2014/0180361 A1* | 6/2014 | Burdick | A61N 1/0553 607/49 |

* cited by examiner

REHABILITATION DEVICE

The invention pertains to a device for rehabilitating patients especially with peripheral nervous system paralysis.

American patent description no. US 2006/0253052 describes a method of rehabilitating a patient suffering from total or partial paralysis of the peripheral nervous system, manifesting itself by weakened muscular tension or muscular atrophy, which entails the use of feedback in which the patient views and/or hears a signal related to the intensity of electromyographic (EMG) activity the patient produces in the appropriate muscles while attempting to move them. The method is intended mostly for highly disabled patients as an alternative for therapy using the AMES method.

American patent description no. US 2004/0106881 describes a powered device, which worn about a patient's elbow or other joint, senses relatively low level signals in the vicinity of the joint generated by a patient having spinal cord or other nerve damage. In response to the relatively low level signals, the powered device moves thus helping the patient to move the joint.

American patent description no. U.S. Pat. No. 5,722,420 describes a method of rehabilitation using closed loop traction force control based on EMG signals from selected muscle. The method is based upon a main traction controller, which uses a high signal-to-noise ratio EMG, which is then scanned and processed into units compatible with computer systems, while adaptively adjusting traction force based on real time detected EMG signals, using biological feedback control by means of visual or audio alarms. The kernel of this solution is its modality which adjusts traction force to the EMG signals detected in real time.

American patent description no. US 2009/0259338 describes a robotic system for rehabilitation using EMG signals, comprising EMG electrodes sequentially connected in series, a DAS card and an additional element connecting to the motor. The electrodes emit an EMG signal making the patient's muscles of the suffering joint contract, which are then measured as input and sent to the control portion of the DAS card. The control portion uses the EMG signals to calculate an appropriate moment to apply an impulse to the suffering joint to make it move.

The main aim of the hereby invention is the construction of a device enabling simultaneous rehabilitation of a few patients with peripheral nervous system paralysis by a single physiotherapist.

The rehabilitation device comprising a remote control terminal, a base, an arm mounted to a column with adjustable height containing an motor propelling the arm and at least two electrodes of the electromyograph (EMG) sensor according to the invention is characteristic in that the motor enables the arm to move within the angular range of 360°, while the EMG signal from the sensor adopted to connect to the muscle or muscles of the patient is transmitted to the network of the motor controlling module and then further by radio or cable connection to a remote control terminal in a way that allows device to initiate extension movement based on the signal from the EMG sensor Favorably the device comprises in the middle part of the base which is telescopically folded.

Favorably the device comprises the extension that is telescopically folded.

Favorably the device comprises the extension that is detachably mounted on the head.

Favorably the device comprises a force sensor built in between the end of the motor and the extension mounting.

Favorably the device comprises an intermediate module that displays a picture on a screen depending on the movement made by the patient being rehabilitated.

Favorably the device comprises an extension that is exchangeable and its size is adjusted to rehabilitating a specific limb.

Favorably the device comprises the detachable extension that has an electronic module which enables device to identify extension.

Favorably the device comprises the detachable extension there the device has a drive and the data derived from drive movement are passed to the engine control module (2).

Favorably the device comprises the extension that is blocked by an electromagnet device.

Favorably the device comprises the head and the front panel containing on the circumference of blinking LEDs that indicate a current state of the device, range of motion.

The main advantage of the invention is the possibility of individual adjustment of the range (speed) and rotation angle of the extension depending on the force (character) of the signal received from the electromyograph or force sensor and the program set in the remote control terminal. Precise measurement of the EMG signals makes it possible to adjust the exercises perfectly to the specific needs and abilities of the patient. At the same time, by using a remote control terminal which can be connected to more than one control motor, the work of a physiotherapist can be optimized, as it is possible to connect one remote control terminal to a few devices at the same time and s/he is then able to supervise a few devices adjusting their parameters as needed. It not only makes the work more effective but also lowers the cost of rehabilitation. The communication between the remote control terminal and the rehabilitation devices may be direct: by means of a radio or cable connection, or by means of intermediate devices mediating in the exchange of measurement and control data. In particular the intermediate units may be additionally responsible for storing, visualizing or emergency control.

The device according to the invention makes it possible to adjust the range (speed) and the rotation angle of the extension to the force (character) of the signal received from the electromyograph sensor and the program set in the remote control terminal. The openings made in the head from the side of the extension on the circumference of the column crown after insertion of pins mechanically block the range of movement of the extension.

Mounting the base on at least three wheels and the use of telescopically folded extension of the base detachable from the column ensures a wide range of rotation which makes rehabilitation of practically any joint possible. At the same time it is characteristic of the invention that there may be a force sensor built in between the motor and the mounting of the extension, which adjusts the movement of the motor to the force generated by the user's limb, which supports its movement. In particular such feedback may generate dynamic resistance, demanding from the user a specifically defined force value. The device also makes it possible to display, by means of an intermediate module, a specific picture on the screen, which depends on the movement made by the person being rehabilitated.

The hereby device, by using electromyograph to measure the level of muscular tension and software to transform the results into the movement of the device supporting the mechanical movement of the limb within the range dependent on the EMG level, enables effective muscular rehabilitation. At the same time, by using the telescopically folded extension mounted on a column with adjustable height the device may be adjusted to any patient's individual needs for the rehabilitation of both upper and lower limbs. In particular, extensions mounted on the column are adjusted to a specific joint and may be exchanged depending on the rehabilitated limb.

The subject of the invention in one embodiment is presented in the drawing where:

EMBODIMENT 1

Figure 1:
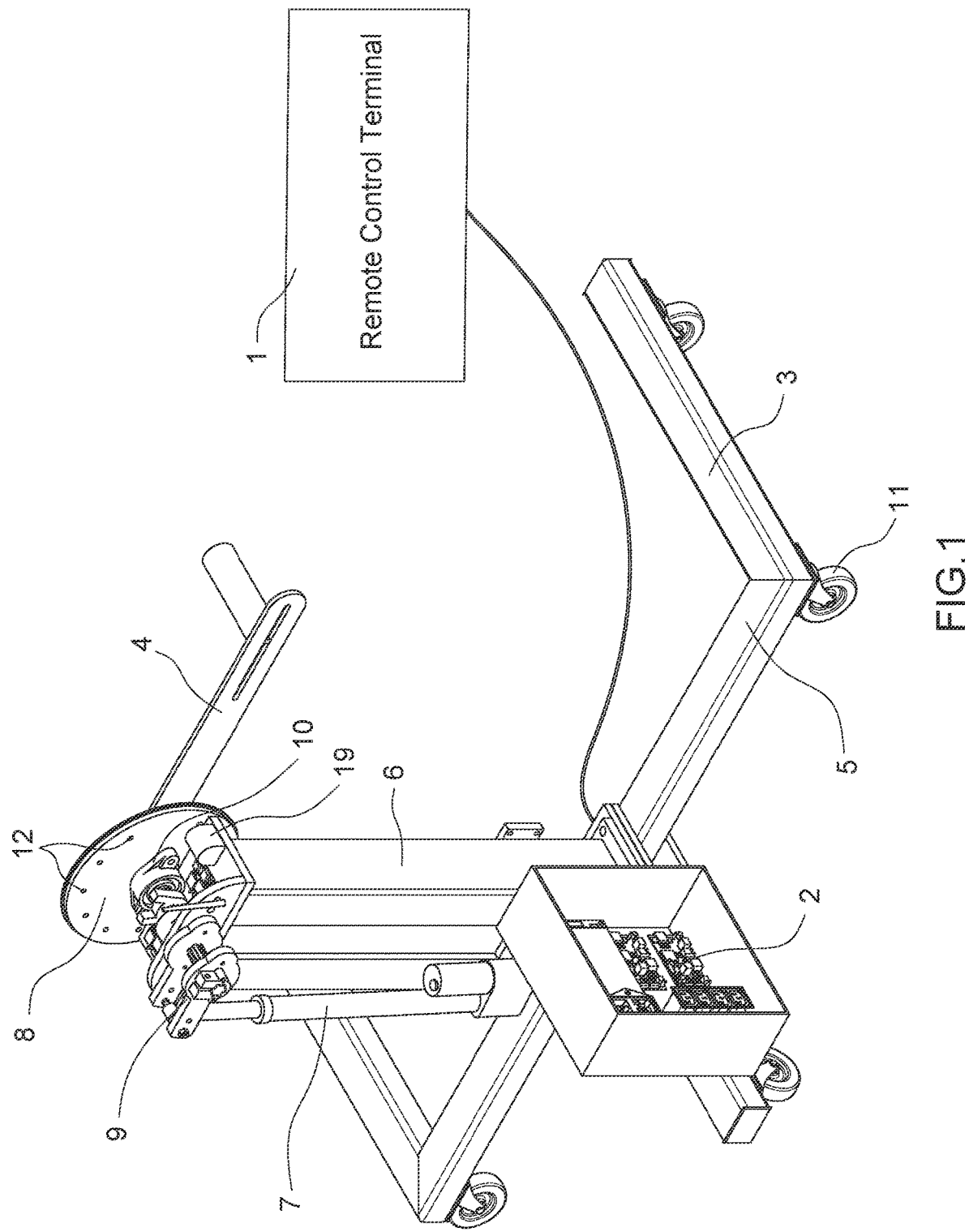
FIG. 1 shows a diagram of the rehabilitation device in a perspective view.
Figure 2:
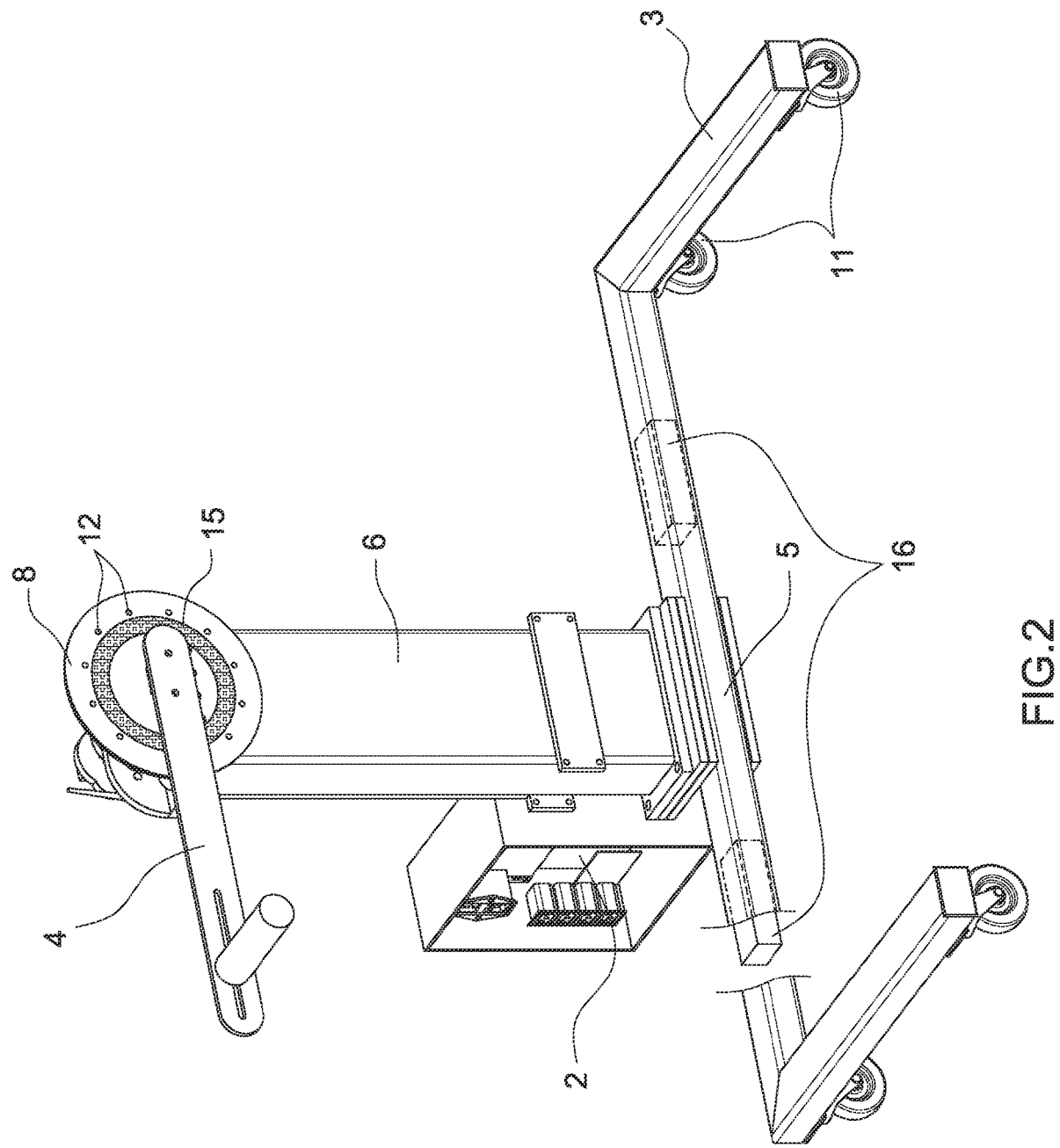
FIG. 2 shows a diagram of the rehabilitation device in the alternative perspective view.
Figure 3:
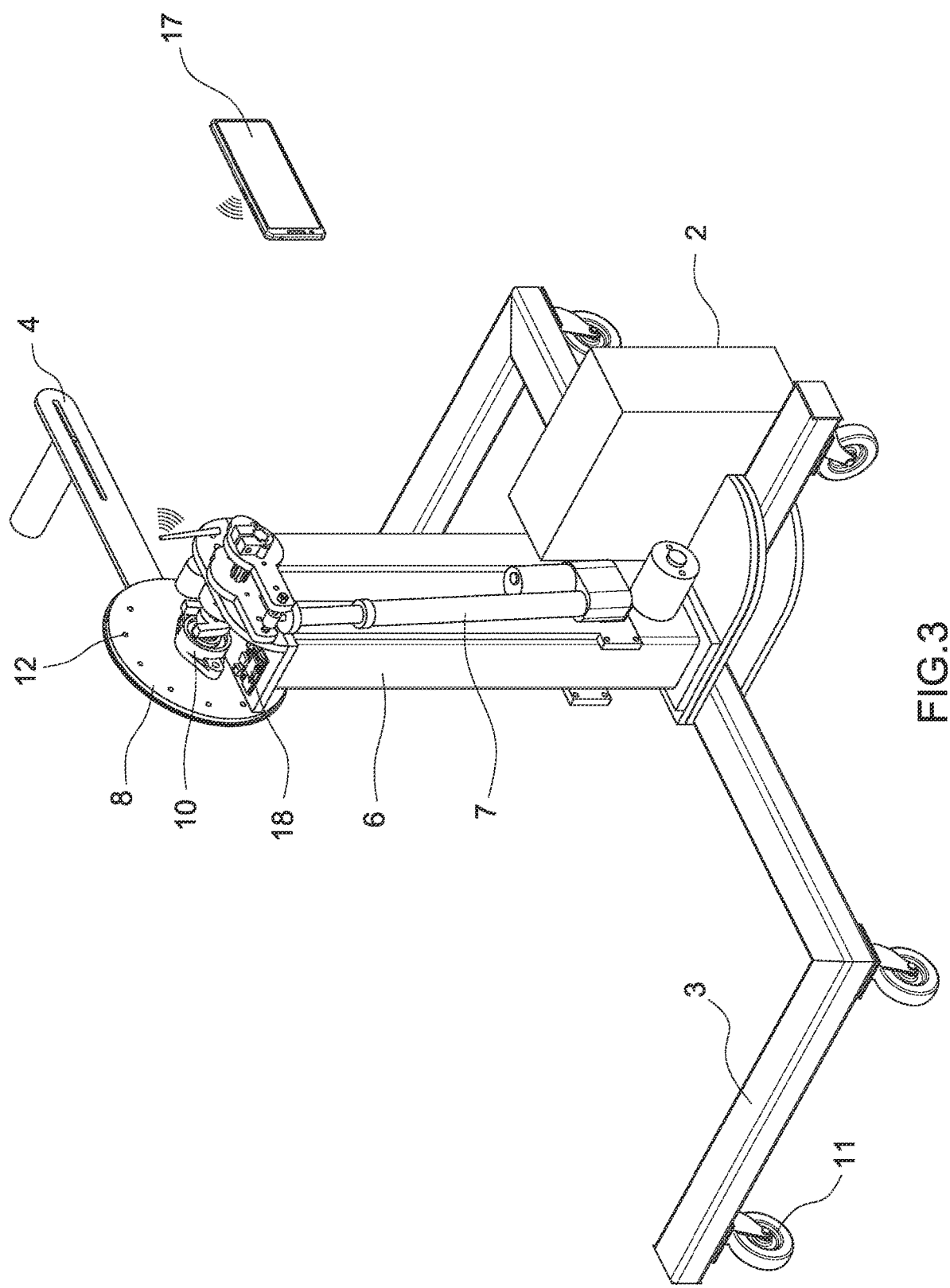
FIG. 3 shows a diagram of the rehabilitation device in the different perspective view.

A rehabilitation device comprising a remote control terminal 1, a base 3, an extension 4 mounted to a column 8 with adjustable height containing an motor 7 propelling the extension 4 moving within the angular range of 360° and at least two electrodes of the electromyograph (EMG) sensor 10. The EMG signal from the sensor connected to the muscle or muscles of the patient is transmitted to the network of the motor controlling module and to a remote control terminal 1 regulating the adjustment of the range of movement to the muscular tension thus programming the movement of the extension on a set radius within the range of 360° while the range (speed) and angle of rotation of the extension 4 depends on the force (character) of the signal received from the electromyograph sensor 10 and the program set in the remote control terminal 1. In the head 8 of the device, from the side of the extension 4, on the circumference of the column crown 6, there are openings 12 to enable mechanical blocking of the movement of the extension 4. Between the end of the motor 7 and the mounting of the extension 4 there is a built-in force sensor 9. The base 3 is mounted on three wheels 11 and its middle part 5 is telescopically foldable.

EMBODIMENT 2

The device comprises of the elements as in embodiment 1 and additionally the extension 4 is telescopically foldable. The extension 4 is detachably mounted on the column 6.

EMBODIMENT 3

A device as described in embodiments 1 and 2 equipped with an additional intermediate module and a monitor where a picture is displayed (e.g.: of a computer game) depending on the movements made by the patient being rehabilitated.

The embodiments presented above do not exhaust the possibilities of using the invention.

The invention claimed is:

1. A rehabilitation device comprising
a remote control terminal, a base,
an extension mounted to a column with adjustable height containing
a motor propelling the extension and at least two electrodes of an electromyography (EMG) sensor, comprising
the motor (7) that enables the extension (4) to move within the angular range of 360°, while an EMG signal from
a sensor adopted to the muscle or muscles of the patient is transmitted to a network of
a motor controlling module (2) and then further by radio or cable connection to a remote control terminal (1) in a way that allows the device to initiate the extension (4) movement based on the signal from the EMG sensor.

2. The device according to claim 1, wherein in the head (8) from the side of the extension (4), on the circumference of the column front plate (6) there are openings (12) for mechanical blocking of the movement of the extension (4).

3. The device according to claim 1, comprising the base (3) that is mounted on at least three wheels (11).

4. The device according to claim 1, comprising the middle part (5) of the base (3) that is telescopically folded.

5. The device according to claim 1, comprising the extension (4) that is telescopically folded.

6. The device according to claim 1, comprising the extension (4) that is detachably mounted on the head (8).

7. The device according to claim 1, comprising a force sensor (9) that is built in between the end of the motor (7) and the extension (4) mounting.

8. The device according to claim 1, comprising an intermediate module that displays a picture on a screen depending on the movement made by the patient being rehabilitated.

9. The device according to claim 1, comprising the extension (4) that is exchangeable and its size is adjusted to rehabilitating a specific limb.

10. The device according to claim 1, comprising the detachable extension (4) that has an electronic module supplied from the device that enables device to identify extension.

11. The device according to claim 1, comprising the detachable extension (4), wherein the extension (4) has a drive and the data derived from drive movement are passed to the engine control module (2).

12. The device according to claim 1, comprising the extension (4) that is blocked by an electromagnetic device.

13. The device according to claim 1, wherein on the front of the head (8) are arranged on the circumference of mechanically or electrically retractable pins (12) for locking the range of movement of the extension (7).

14. The device according to claim 1, wherein in the base (3) are provided loaded and/or replaceable batteries supplying the device.

15. The device according to claim 1, wherein the device has a built-in wireless communication module to identify a user.

16. The device according to claim 1, comprising the head (8) and the front panel containing on the circumference of blinking LEDs that indicate a current state of the device and range of motion.

* * * * *